United States Patent [19]

Chafin et al.

[11] Patent Number: 4,600,536

[45] Date of Patent: Jul. 15, 1986

[54] EXPLOSIVE COMPOUND

[75] Inventors: Andrew P. Chafin, Levittown, Pa.; Arnold T. Nielsen, Ridgecrest, Calif.

[73] Assignee: The United States of America as represented by the Secretary of the Navy, Washington, D.C.

[21] Appl. No.: 662,868

[22] Filed: Oct. 19, 1984

[51] Int. Cl.[4] .............................................. C07C 117/00
[52] U.S. Cl. ...................................... 260/349; 149/105
[58] Field of Search .......................................... 260/349

[56] References Cited

U.S. PATENT DOCUMENTS 1,824,848  9/1931  Turek ............................... 260/349 X
3,948,957  4/1976  Beck .................................... 260/349
4,262,148  4/1981  Nielsen et al. ....................... 568/932

OTHER PUBLICATIONS

Patai, et al., "The Chemistry of Halides Pseudo-Halides and Azides", Part 1, (1983), p. 344, John Wiley & Sons, N.Y.
Boyer, et al., Chemical Reviews, 54, (1954), pp. 2 and 8.

Primary Examiner—Joseph Paul Brust
Attorney, Agent, or Firm—Robert F. Beers; W. Thom Skeer

[57] ABSTRACT

A new polynitro compound pentanitrophenyl azide is disclosed, and a method of preparation is disclosed wherein hexanitrobenzene is reacted with sodium azide. This new polynitro compound is useful as an explosive.

2 Claims, No Drawings

EXPLOSIVE COMPOUND

BACKGROUND OF THE INVENTION

1. Field of the Invention

This invention relates to a composition of matter and a method for producing the same, and is particularly related to a polynitro compound used as an explosive.

2. Description of the Prior Art

Many useful explosives contain nitro groups. However, there are few practical synthetic methods available for introduction of a nitro group attached to a carbon into an organic molecule. Known methods such as nitration, peroxytrifluoroacetic acid oxidation of amines, oximes and hydroxylamines or reactions of halides with nitrite ion, all have limitations.

In particular, there are very few methods broadly applicable to the synthesis of polynitro compounds.

SUMMARY OF THE INVENTION

An object of the present invention is to provide a new polynitro compound and a method of synthesis. The compound pentanitrophenyl azide is prepared by reacting hexanitrobenzene and sodium azide.

DESCRIPTION OF THE PREFERRED EMBODIMENT

The reaction of hexanitrobenzene with an azide ion has been found to yield a powerful new explosive, pentanitrophenyl azide in a high yield.

The reaction is conducted by stirring a benzene solution of hexanitrobenzene with a slight excess of sodium azide (aqueous solution) at 25° C. After separating and drying the benzene solution, the solvent is removed leaving pure pentanitrophenyl azide. Recrystallization from carbon tetrachloride gives either long, flat yellow prisms (α-form) or chunky, orange-yellow rosettes (β-form) of pentanitrophenyl azide.

The properties of both forms are listed in the following table:

| TABLE OF PROPERTIES | | |
|---|---|---|
| Property | Alpha | Beta |
| Impact sensitivity, $H_{50}$, 2.5 Kg wt, cm | 43 | 17 |
| Density, g/cm$^3$ | 1.76 | 1.79 |
|  | 1.88[a] | 1.88[a] |
| Detonation velocity, mm/μs | 8.67[b] | 8.78[b] |
|  | 9.21[c] | 9.21[c] |
| Detonation pressure, Kbar | 329[b] | 341[b] |
|  | 404[c] | 404[c] |
| Melting Point, °C. | 120 | 120 |
| Decomposition Temperature | 120 | 120 |

[a]calculated by Holden's method
[b]calculated from the heat of formation by Kamlet's method
[c]calculated by Rothstein's method The most notable property of pentanitrophenyl azide is its brisance. The steel anvils employed in the impact test are significantly dented by the explosion, in contrast to the behavior of most explosives. A typical result in this test is the formation of no dent whatsoever, as with cyclotetramethylenetetranitramine (HMX).

The two crystalline forms of pentanitrophenyl azide exhibit significantly different impact sensitivities. Their densities are similar and lower than calculated by Holden's method. The explosive is quite energetic and comparable to cyclotrimethylenetrinitramine (RDX).

The alpha form of pentanitrophenyl azide is unusually insensitive for such a powerful explosive. It decomposes at its melting point which is lower than that of RDX and HMX. Owing to the decomposition on melting, it would not be possible to melt cast the material. Pentanitrophenyl azide can be prepared by carrying out the procedure set forth in the following specific example.

EXAMPLE

Hexanitrobenzene (2.00 g) is dissolved in 75 ml of benzene. Sodium azide (0.411 g) in 45 ml of water is added and the mixture is stirred vigorously for 90 minutes, at 25° C. The benzene layer is then separated, dried with magnesium sulfate, and concentrated to dryness. The yield of crude pentanitrophenyl azide is 1.87 g (95%).

Recrystallization from a hot saturated carbon tetrachloride solution yields 0.82 g of the alpha form, long flat yellow prisms, having a melting point of 119.5–121° C.

Analysis calculated for $C_6N_8O_{10}$: C, 20.94%; N, 32.56%. Found: C, 20.88%; N, 32.37%; H, 0.07%.

The beta form can be obtained as chunky orange-yellow rosettes by recrystallization from dilute carbon tetrachloride solution, and has a melting point of 120–121° C.

Both alpha and beta forms may also be obtained by seeding a warm saturated solution of carbon tetrachloride and of the crude pentanitrophenyl azide, with the appropriate crystals.

What is claimed is:

1. A method for producing alpha-pentanitrophenyl azide comprising the steps of:
   dissolving pentanitrophenyl azide in carbon tetrachloride to form a saturated solution; and
   recrystallizing to yield the alpha product.

2. A method for producing beta-pentanitrophenyl azide comprising the steps of:
   dissolving pentanitrophenyl azide in carbon tetrachloride to form a dilute solution; and
   recrystallizing to yield the beta product.

* * * * *